United States Patent [19]

Armstrong

[11] 4,332,890

[45] Jun. 1, 1982

[54] DETECTION OF *NEISSERIA GONORRHOEAE*

[75] Inventor: Alan S. Armstrong, Waukegan, Ill.

[73] Assignee: Abbott Laboratories, North Chicago, Ill.

[21] Appl. No.: 905,575

[22] Filed: May 15, 1978

[51] Int. Cl.³ .............................................. C12Q 1/66
[52] U.S. Cl. ..................................... 435/7; 23/230 B; 424/12; 435/34; 435/871
[58] Field of Search ................ 195/103.5 A, 103.5 M, 195/103.5 R; 23/230 B; 424/12, 13; 435/7, 34, 871

[56] References Cited

U.S. PATENT DOCUMENTS

| | | | |
|---|---|---|---|
| 3,096,250 | 7/1963 | Ingraham | 195/103.5 A X |
| 3,951,748 | 4/1976 | Devlin | 424/12 X |
| 4,029,756 | 6/1977 | Gaafar | 23/230 B X |
| 4,066,744 | 1/1978 | Price et al. | 424/12 |
| 4,067,959 | 1/1978 | Bolz | 195/103.5 A X |
| 4,140,581 | 2/1979 | Weetall | 195/103.5 A |
| 4,142,939 | 3/1979 | Morse et al. | 195/103.5 A X |

*Primary Examiner*—Robert J. Warden
*Attorney, Agent, or Firm*—Steven M. Odre; John J. McDonnell

[57] ABSTRACT

A procedure for detection of *Neisseria gonorrhoeae* in a microbial growth culture. Lysates of the suspect organism are tested by reverse passive hemagglutination with particles sensitized with antibodies to eleven *N. gonorrhoeae* strains, ATCC 31397, 31398, 31399, 31400, 31401, 31402, 31403, 31404, 31405, 31406, and 31407.

2 Claims, No Drawings

DETECTION OF *NEISSERIA GONORRHOEAE*

BACKGROUND OF THE INVENTION

The present invention relates generally to methods and materials for detection of *N. gonorrhoeae* in a microbial growth culture and more specifically relates to a rapid and reproducible reverse passive hemagglutination (RPHA) test for any of the known strains of the organisms.

Presently available procedures for identification of *N. gonorrhoeae* in a culture medium, e.g., Thayer-Martin agar, involve preliminary screening on the basis of source, morphology, gram stain and oxidase testing. Oxidase-positive gram-negative diplococci exhibiting typical colonial morphology on Thayer-Martin medium seeded from the genitourinary tract of a patient are considered presumptively gonococci. Confirmation of this preliminary determination conventionally involves examination of the organism within the framework of additional test schemes specifically directed to the detection of *N. gonorrhoeae* as opposed to other organisms displaying similar characteristics. Such specific tests include carbohydrate degradation screening which requires approximately 48 hours to complete and is sometimes unreliable owing to the fact that some strains of *N. gonorrhoeae* may either fail to grow or may give false negative sugar reactions. An alternative commercial screening procedure involves the use of fluorescent antibodies and, while the procedure is relatively rapid and specific for all *N. gonorrhoeae* strains, the use of a rather expensive fluorescence microscope by a highly skilled technician is required for the determination. See, e.g., *Health Laboratory Science*, Vol. 12, No. 3, pp. 215–218 (1975).

While it was generally known that RPHA testing for confirmation of microorganisms is faster and more reproducible than, e.g., carbohydrate degradation analysis, such procedures have been believed to be inappropriate to screening for *N. gonorrhoeae* owing to the frequently acute specificity of antibodies to the different strains of *N. gonorrhoeae*. It was generally thought, for example, that a great number of assays involving a similarly large number of specific antibodies might be necessary to dispositively characterize an organism as one of the many *N. gonorrhoeae* strains.

The art, therefore, presently has a need for a rapid, reproducible method for identification of the presence of *N. gonorrhoeae* which does not involve the tedious or expensive procedures of conventional methods.

BRIEF DESCRIPTION

The present invention provides new methods and materials for a reverse passive hemagglutination test useful in the detection of *N. gonorrhoeae* from microbial growth on Thayer-Martin agar medium or other comparable media.

According to the present invention, antibodies derived from the use of eleven *N. gonorrhoeae* strains, ATCC 31397, 31398, 31399, 31400, 31401, 31402, 31403, 31404, 31405, 31406, and 31407 as immunogens are employed to sensitize immunologically inert particles (e.g., stabilized erythrocytes) and employed in an RPHA assay to effectively identify the presence of any one or more of the known *N. gonorrhoeae* strains. The procedure is not subject to false positive reactions by organisms ordinarily interfering with antibody-oriented screening for *N. gonorrhoeae*.

Briefly stated, antibodies to each of the abovementioned strains are pooled and employed to sensitize discrete carrier particles. The reagent particles, in turn, are employed in a hemagglutination assay with lysate of suspected cultured cells to verify the presence or absence of *N. gonorrhoeae*. The entire system employs a minimum of equipment and provides accurate results in as little as three hours.

Numerous aspects and advantages of the present invention will be understood by those skilled in the art upon consideration of the following detailed description.

DETAILED DESCRIPTION

The eleven *N. gonorrhoeae* strains employed in the practice of the present invention are each susceptible to the following taxonomic description.

Order: Eubacteriales
Family: Neissericeae
Genus: Neisseria
Species: Gonorrhoeae
Morphology: Gram negative spherical or bean shaped diplococci with adjacent sides flattened usually $0.6 \times 1.0\mu$ and more uniform in size.

Biochemical and Cultural: Aerobic, optimal growth requires 4–10% $CO_2$ and incubation at 36° C.

The cultures grow slowly on Thayer-Martin, producing small, barely visible colonies after 24 hours (0.1 mm in diameter) with typical morphology seen on 48–72 hours cultures. The colonies are small, 1.0 mm in diameter, gray white, transparent, smooth, with round entire edge, glistening surface and butyrous consistency.

Oxidase+, catalase+, ferments glucose but not maltose, lactose or sucrose.

Virulence: All eleven strains were originally isolated from patients with symptomatic gonorrhea.

According to the invention, each of the eleven strains is employed as an immunogen in the serial immunization of an animal. A pool of serums is prepared by combining immune serum from the several animals each immunized with a single strain to yield a combination of serums containing antibodies to all of the strains. This pool of antiserums is passed over an immunoadsorbent column containing cell walls or extracts of the strains employed to generate the immune serums. Antibodies bound to cell walls are then eluted by chemical means. Preferably, the antibodies are additionally absorbed with selected strains of *N. meningitidis* to eliminate antibodies reactive with *Neisseria* species other than *N. gonorrhoeae*. Alternatively, each individual antiserum may be passed over a column containing cell walls or extracts of the particular strain employed as an immunogen in development of the antiserum, eluted, absorbed against *N. meningitidis* and then pooled.

The pooled antibodies so obtained are employed to coat or sensitize discrete particles of immunologically inert material such as stabilized human type O erythrocytes. Organisms suspected to be *N. gonorrhoeae* are removed from their growth medium and a suspension of organisms is prepared in water to a standard turbidity (as measured by optical density) and subsequently treated to develop a lysate test material. The test material is contacted with the antibody-sensitized particles and an agglutination reaction confirms the presence of *N. gonorrhoeae*.

The illustrative examples set out below are directed to the following aspects of practice of the invention: (a) isolation of N. gonorrhoeae cell walls; (b) preparation of N. gonorrhoeae cell wall phenol extract; (c) preparation of inactivated N. meningitidis; (d) preparation of stabilized erythrocyte carrier particles; (e) preparation of carrier particles sensitized with N. gonorrhoeae phenol extract; (f) preparation of immunoadsorbent column; (g) preparation of N. gonorrhoeae antiserum; (h) isolation of N. gonorrhoeae antibodies; (i) absorption of N. gonorrhoeae antibody preparation with inactivated N. meningitidis; (j) preparation of reagent carrier particles sensitized with N. gonorrhoeae antibodies; (k) preparation of bacterial lysate; (l) RPHA test for N. gonorrhoeae; and (m) verification testing of specificity of reagent.

N. gonorrhoeae strains ATCC 31397, 31398, 31399, 31400, 31401, 31402, 31403, 31404, 31405, 31406, and 31407 have been deposited by applicant and are available from the American Type Culture Collection, 12301 Parklawn, Rockville, Md. 20852.

EXAMPLE 1

Isolation of N. gonorrhoeae Cell Walls

The following procedure is employed to develop a cell wall preparation for each of the eleven N. gonorrhoeae strains, ATCC 31397, 31398, 31399, 31400, 31401, 31402, 31403, 31404, 31405, 31406, and 31407. The strain is cultivated on Thayer-Martin medium and removed from the agar by washing with 0.01 M phosphate buffered normal saline, pH 7.2 (PBS). The cells are recovered by centrifugation a 16,300×g for 40 minutes at 4° C., washed once with normal saline, and made up into a 20% (weight/volume) suspension in distilled water. Cells are disrupted with glass beads (approximately 150 to 200μ) in a homogenizer cooled with liquid carbon dioxide. Cell walls are separated from the glass beads using a sintered glass funnel and resuspended in distilled water. After centrifugation at 9,750×g for 18 hours at −20° C., the pellet may be stored at 4° C.

EXAMPLE 2

Preparation of N. gonorrhoeae Cell Wall Phenol Extract

Equal weights of wet packed cell walls of the eleven strains prepared according to Example 1 are combined and made up to a 20% (weight/volume) suspension in distilled water. The suspension is extracted with an equal volume of 90% phenol in water and 0.1 M sodium acetate buffer, pH 5.0, containing 0.5% naphthalene disulfonic acid and 0.5% sodium dodoecyl sulfate at 70° C. for 20 minutes. The phases are separated and recovered by centrifugation at 175×g for 30 minutes. The phenol phase is dialyzed for 3 days at 4° C. against frequent changes of distilled water. The extract is clarified by centrifugation at 16,300×g for 30 minutes at 4° C., passed through a 0.45 μm membrane filter, and stored at 4° C.

EXAMPLE 3

Preparation of Inactivated N. meningitidis

N. meningitidis, Group A, Strain MK01A (Naval Medical Research Unit No. 4, Great Lakes, Ill.); Group B, Strain 3951 (King County Department of Health, Seattle, Wash.), and Group B, Strain 5066-335 (Naval Medical Research Unit No. 4, Great Lakes, Ill.) are each grown on Mueller-Hinton broth at 37° C. for 18 hours in a gyratory shaker. The organisms are separately pelleted at 16,300×g for 30 minutes at 4° C. and washed three times by centrifugation with equal volumes of PBS. Cells are resuspended to one-fifth the original broth (generally 1 liter) volume, placed in a Pyrex dish and sealed in a plastic bag containing a cotton-plugged port. The cells are inactivated with ethylene oxide and stored at 4° C. (Failure to grow on Mueller-Hinton agar was evidence of inactivation.)

EXAMPLE 4

Preparation of Stabilized Erythrocyte Carrier Particles

Human erythrocytes are stabilized according to the method of Hirata, et al., [Journal of Immunology, Vol. 100, No. 3, pp. 641–646 (1968); U.S. Pat. Nos. 3,714,345; 3,715,427; and/or 3,925,541]. Briefly re-stated, the procedure is as follows. A suspension of washed erythrocytes is prepared in a neutral buffering solution in a concentration of about 10% on a volume basis and treated with a small amount, preferably from 1.5 to 5% by volume of pyruvic aldehyde, relative to the volume of erythrocytes, for a time sufficient to impart stability to the erythrocytes, preferably for from 12 to 24 hours. The erythrocytes are then washed several times to remove excess pyruvic aldehyde and any other materials which may have originated from the serum. The pyruvic aldehyde-treated erythrocytes are treated with a small amount, preferably from 1.5 to 5% by the volume of formaldehyde, relative to the volume of erythrocytes, for from 12 to 24 hours and the excess formaldehyde is removed by washing with a buffered solution.

EXAMPLE 5

Preparation of Carrier Particles Sensitized with N. gonorrhoeae Phenol Extract

Stabilized erythrocytes are prepared according to Example 4 and stored at 10% (weight/volume) concentration in 0.11 M phosphate buffer, pH 7.2 (PB). Coating of the particles is accomplished, e.g., by mixing: 2 ml of the phenol extract of Example 3; 20 ml of 0.1 M sodium acetate buffer, pH 4.0; 1 ml aqueous chromic chloride (10 mg CrCl. 6 $H_2O$/ml); and the pellet formed by centrifugation of 2 ml of the above 10% suspension of stabilized erythrocytes at 700×g for 3½ minutes. After mixing, the suspension is incubated at 37° C. for 30 minutes with agitation briefly after 15 minutes to minimize settling of erythrocytes. The sensitized cells are washed four times by centrifugation at 700×g for 2 minutes at 25° C. with ten times the erythrocyte volume of PB. The cells are resuspended to 1% (weight/volume) in PB containing 0.2% sucrose and 10% bovine serum albumin and stored at −30° C.

EXAMPLE 6

Preparation of Immunoadsorbent Column

The following procedure may be employed to develop eleven columns each consisting of one of eleven distinct gels correlated to the eleven strains of N. gonorrhoeae employed. (An equivalent procedure may be employed to entrap cell walls of all eleven strains in a single gel for preparation of a single, large column.) Eight ml of each of the eleven 20% (weight/volume) cell wall suspensions prepared according to Example 1 is added to 20 ml of a gel consisting of 10% total monomer [acrylamide and N,N'-methylenebis-acrylamide (BIS) of which 25% is BIS] together with 40 μl of N,N,N,N-tetramethylethylenediamine and 2.0 ml of a freshly prepared 40% aqueous solution of ammonium persulfate. Each gel is allowed to polymerize at room temperature for about 30 minutes and is then broken into small pieces by passing through an 18 gauge needle attached to a 50 ml syringe. The particles are washed with 100 ml of 0.1 M Tris (hydroxymethyl) aminoethane-hydrochloride buffer, pH 7.5, containing 0.15 M NaCl (THS), followed by 100 ml of 0.1 M glycine-hydrochloride buffer, pH 2.3, containing 0.15 M NaCl (GHS) and finally with 100 ml THS. Two grams of BioGel P-100 (Bio-Rad Laboratories, Richmond, Calif.) swollen in THS overnight is packed into a 2×36 cm chromatographic column followed by addition of the immunoadsorbent particles. The entire column was then washed again with THS, GHS and THS as above.

EXAMPLE 7

Preparation of N. gonorrhoeae Antiserum

Colony types 3 and 4 of the eleven N. gonorrhoeae strains are grown on Thayer-Martin agar for 18 hours at 37° C. in a candle jar and each strain is employed to generate an antiserum as follows. The colony is removed from the agar with 0.01 M phosphate-buffered saline (PBS), pH 7.2, washed three times by centrifugation at 3000×g for 15 minutes at 4° C., and resuspended in PBS. Turbidity is adjusted to develop two concentrations ("1×" and "10×") having respective optical densities of 0.52 and 5.2 at 630 nm and these are stored at −20° C. New Zealand white rabbits are immunized at multiple sites with 10 ml of a homogenized inoculant comprising equal volumes of thawed 10× bacterin suspension and Freund's Complete Adjuvant. At approximately 7, 10 and 15 days after initial inoculation, the rabbits are respectively injected with 0.5 ml, 1.0 ml and 2.0 ml of thawed 1× bacterin. Two additional 2.0 ml injections of the 1× bacterin are thereafter made at approximately 5 day intervals. Four to six days later whole blood samples are withdrawn and evaluated (see below) for potency of antibodies using particles according to Example 5 sensitized with a phenol extract of cell walls of the strain inoculated. Animals providing samples showing desired potency are then bled and the antiserum pooled and stored. Animals providing samples showing less than desired potency are again inoculated twice, with a 5 day interval, with 2.0 ml of the 1× bacterin, after which another blood sample is tested for antibody potency. The animal is bled if the desired potency is observed and the serum stored.

Potency of antiserum is evaluated by passive hemagglutination using the phenol extract-sensitized particles of Example 5. A diluent for the antiserum is prepared by adding 0.1% gelatin to 0.11 M phosphate buffer, pH 7.2 (PB), followed by heating at 60° C. until the gelatin dissolves and filtration through a 0.45 μm membrane filter. Twenty-five μl of 0.25% (weight/volume) erythrocyte suspension in PB/sucrose/albumin prepared according to Example 5 is added to 25 μl of serial two-fold dilutions of antiserum in plastic "V" bottom microtiter trays. The filled trays are shaken on a vortex mixer for 10 seconds, covered, and allowed to stand overnight at room temperature. The endpoint titer of the sample was designated as the reciprocal of the highest dilution showing an agglutination pattern obviously different from that of the control (25 μl of the 0.25% erythrocyte suspension and 25 μl of the diluent). Table 1 below illustrates reciprocal titers for each of the antiserums of the eleven strains considered to be indicative of suitable antibody potency.

TABLE 1

| ATCC Strain | Titer |
| --- | --- |
| 31397 | 6400 |
| 31398 | 1600 |
| 31399 | 1600 |
| 31400 | 800 |
| 31401 | 800 |
| 31402 | 1600 |
| 31403 | 1600 |
| 31404 | 12800 |
| 31405 | 12800 |
| 31406 | 1600 |
| 31407 | 12800 |

EXAMPLE 8

Isolation of N. gonorrhoeae Antibodies

The following procedure for isolation of individual antibodies from each of the eleven antiserums prepared according to Example 7 may be employed to isolate a "pool" of eleven antibodies by first combining the eleven antiserums and then employing a single immunoadsorbent column containing a gel entrapping cell walls of all eleven N. gonorrhoeae strains.

Seven ml of rabbit antiserum according to Example 7 is applied to a column prepared according to Example 6 containing cell walls of the strain used for immunization. Serum is recycled through the column for about 2 hours using a peristaltic pump having a flow rate of about 100–150 ml/hour. The column is then washed with pH 7.5 THS until absorbance at 280 nm was ≦0.02. The adsorbed antibodies are then eluted with pH 2.3 GHS. Fractions of from 2 to 2.5 ml are collected and, if necessary, immediately adjusted to from about pH 6.9 to pH 7.1 using a 0.5 M sodium carbonate buffer, pH 9.5. Consecutive fractions having absorbance at 280 nm of ≧0.1 are pooled, dialyzed against normal saline at 4° C. overnight, concentrated under negative pressure dialysis at room temperature, re-dialyzed and stored at 4° C.

EXAMPLE 9

Absorption of N. gonorrhoeae Antibody Preparation with Inactivated N. meningitidis A suspension of inactivated N. meningitidis (6 ml Group B, Strain 5066-355; 6 ml Group A, Strain MK01A; and 0.6 ml Group B, Strain 3951) is centrifuged at 16,300×g for 1 hour at 4° C. Six ml (150 μg/ml) of antibody prepared according to Example 8 is added to the pellet, slurried and agitated gently on a vortex mixer for 1 hour at room temperature. After centrifugation at 16,300×g for 1 hour at 4° C. the absorbed antibody is stored at 4° C.

EXAMPLE 10

Preparation of Reagent Carrier Particles Sensitized with N. gonorrhoeae Antibodies Stabilized erythrocyte carrier particles prepared according to Example 4 may be sensitized with a pool of the eleven antibodies prepared according to Examples 8 and 9 by the following procedure. To a 1% (weight/volume) suspension of stabilized erythrocytes in 0.01 M sodium acetate buffer, pH 4.0, is added from 1.0 to 10.0 μg of pooled antibody preparation per ml of suspension. Fifty to 500 μg of $CrCl_3 \cdot 6H_2O$ (10 mg/ml previously dissolved in 0.01 M sodium acetate buffer, pH 4.0), the suspension is mixed briefly on a vortex mixer and incubated for 30 minutes at 30° C. with an intermediate mixing after 15 minutes to minimize settling of the erythrocytes. The suspension is washed in 0.1 M phosphate buffer, resuspended in 1% suspension of 0.11 M phosphate buffer, pH 7.4, containing 2% sucrose and 10% bovine serum albumin, and stored. The particular concentration of pooled antibody preparation and chromic chloride yielding the highest titer against homologous bacterial lysates and lowest titer against heterologous lysates are selected and designated as optimal coating conditions for the antibody pool. Sensitized reagent particle suspensions may be lyophilized and stored for 12 to 18 weeks without loss of activity.

EXAMPLE 11

Preparation of Bacterial Lysates

Lysates of bacteria for use in RPHA assays according to the invention are prepared as follows. Organisms are incubated on appropriate media for 18 hours, after which colonies are removed with a swab and suspended in a distilled water solution of 20% glycerin. The suspension is agitated vigorously to break up clumps and adjusted to give an optical density of 0.52 at 630 nm. (Suspensions so formed may be frozen and stored for up to several weeks at −30° C.) The suspension is diluted 1:10 with distilled water and treated, for example, with 30 μl of 1 N sodium hydroxide per ml of suspension. The treated suspension is briefly agitated to enhance lysis. Such preparations are ready for use in 15 minutes and may be employed for up to 4 hours after preparation if held at 2° to 27° C. It is noteworthy that all strains of N. gonorrhoeae will generally provide suspensions which clear (are not turbid or hazy compared with a water blank) within about 1 minute of alkaline treatment. A suspension which does not clear may generally be ruled out as N. gonorrhoeae.

EXAMPLE 12

RPHA Test for N. gonorrhoeae

A reverse passive hemagglutination assay for suspected N. gonorrhoeae is carried out as follows. A gelatin/phosphate buffer diluent is prepared in the manner set out in Example 8. The test is performed with a standard microtiter "V" plate. One drop of diluent is added to the wells, followed by 5 μl of the sample alkaline lysate, prepared according to Example 11. One drop of uniformly suspended sensitized carrier particles [0.1% (weight/volume) suspension of cells prepared according to Example 10] is added to each well containing the lysate as well as to a few wells containing diluent alone (cell control). The plate is covered and its edge is tapped repeatedly to thoroughly mix the reactants. The assay mixture is incubated at room temperature on a non-vibrating level surface and read after 3 and up to 24 hours. A positive test is indicated by the formation of a disperse settling pattern of sensitized carrier particles and a negative test is indicated by formation of a compact button of particles comparable to the cell control.

EXAMPLE 13

Verification Testing of Specificity of Reagent

The sensitivity of an RPHA assay employing reagents of the invention is verified by the results of screening of seventy-nine randomly selected N. gonorrhoeae strains from widely varying sources. All strains which were confirmed as positive for N. gonorrhoeae by the fluorescent antibody test [see, Health Laboratory Science, Vol. 12, No. 3, pp. 215–218 (1975)] also gave positive tests when subjected to RPHA assays according to Example 12. Table 2 below relates the results of the sensitivity screening.

TABLE 2

| N. gonorrhoeae Strain Source | No. Tested | Confirmed as Positive Fluoresecent Antibody | RPHA |
| --- | --- | --- | --- |
| Seattle, Wash. | 20 | 20 | 20 |
| Milwaukee, Wis. | 19 | 19 | 19 |
| Chicago, Ill. | 17 | 17 | 17 |
| Lake County, Ill. | 8 | 8 | 8 |
| Atlanta, Ga.[a] | 7 | 7 | 7 |
| Seattle, Wash.[a] | 2 | 2 | 2 |
| Europe | 6 | 6 | 6 |

[a]Penicillinase producers

The specificity of the RPHA assay of the invention for N. gonorrhoeae is verified by the results of testing on numerous nongonococcal Neisseria species. All species which failed N. gonorrhoeae confirmation by fluorescent antibody and carbohydrate degradation assays also were negative when subjected to RPHA assay. Table 3 relates the results of the specificity screening.

TABLE 3

| Species | No. Tested | Absence of Confirmation Fluorescent Antibody | Carbohydrate | RPHA |
| --- | --- | --- | --- | --- |
| N. meningitidis (Group A) | 1 | 1 | 1 | 1 |
| N. meningitidis (Group B) | 2 | 2 | 2 | 2 |
| N. meningitidis (Group C) | 1 | 1 | 1 | 1 |
| N. meningitidis (untyped) | 4 | 3[b] | 4 | 4 |
| N. lactamica | 5[a] | 5 | 5 | 4[a] |
| N. sicca | 13 | 13 | 13 | 13 |
| N. perflava | 3 | 3 | 3 | 3 |
| B. catarrhalis | 1 | 1 | 1 | 1 |

[a]One strain failed to lyse completely and was not RPHA tested.
[b]One strain not subjected to fluorescent antibody assay.

The specificity of the RPHA assay of the invention for N. gonorrhoeae is additionally verified by the results of testing on numerous non-Neisseria organisms. All organisms generated a negative assay in the RPHA procedure. Table 4 below relates the results of the specificity screening.

TABLE 4

| Organism | No. Tested | Negative RPHA |
| --- | --- | --- |
| Acinetobacter sp. | 5 | 5 |
| Candida sp. | 1 | 1 |
| Flavobacterium sp. | 2 | 2 |
| Bacillus sp. | 1 | 1 |
| Lactobacillus sp. | 3 | 3 |
| Moraxella sp. | 4 | 4 |
| Corynebacterium sp. | 7 | 6[a] |
| Enterococci | 3 | 3 |
| Proteus sp. | 4 | 4 |
| Staphylococcus epidermis | 6 | 6 |
| Streptococci (viridans) | 2 | 2 |
| Staphylocuccus aureus | 12 | 11[a] |
| Homophilus influenzae | 5 | 5 |
| Streptococci (Group A) | 4 | 4 |
| Salmonella sp. | 5 | 5 |
| Shigella sp. | 5 | 5 |

[a]One strain failed to lyse completely and was not RPHA tested.

Numerous modifications and variations in practice of the invention are expected to occur to those skilled in the art upon consideration of the foregoing detailed description. As one example, while stabilized human erythrocytes provide a preferred particulate carrier for practice of the invention, numerous other carriers such as polystyrene latex, bentonite, charcoal, cholesterol, and lecithin particles may be employed. As another example, while alkaline bacterial lysates are preferred as a material for testing, lysates developed through other chemical or physical treatment (e.g., treatment with sodium dodoecyl sulfate or freeze-thawing or sonication) are expected to be equally suitable for use in the practice of the invention.

In a like manner, it is contemplated that novel strains of *N. gonorrhoeae* may be isolated from time to time in the future and may not provide lysates which are reactive with the reagent particles of the invention. It is therefore contemplated that an additional antibody specific to such a strain may be added to the pool of eleven antibodies employed to generate reagents according to the invention without departing from the spirit thereof.

What is claimed is:

1. A procedure for identification of a microorganism as *N. gonorrhoeae*, said procedure comprising:
   preparing a lysate of the microorganism;
   contacting a sample of said lysate with a suspension of discrete particles sensitized with antibodies to *N. gonorrhoeae* strains ATCC 31397, 31398, 31399, 31400, 31401, 31402, 31403, 31404, 31405, 31406, and 31407;
   incubating said mixture of lysate and particles; and
   determining the presence of agglutination of said incubated mixture indicative of the positive identification of the microorganism as *N. gonorrhoeae*.

2. A reagent for use in a reverse passive hemagglutination assay for identification of a microorganism as *N. gonorrhoeae*, said reagent comprising:
   a suspension of discrete particles, surface portions of which are sensitized with antibodies to *N. gonorrhoeae* strains ATCC 31397, 31398, 31399, 31400, 31401, 31402, 31403, 31404, 31405, 31406, and 31407.

* * * * *